(12) United States Patent
Tennican

(10) Patent No.: US 10,500,344 B2
(45) Date of Patent: Dec. 10, 2019

(54) INJECTION SYSTEMS WITH STORAGE COMPARTMENTS

(71) Applicant: Hyprotek, Inc., Spokane, WA (US)

(72) Inventor: Patrick O. Tennican, Spokane, WA (US)

(73) Assignee: Hyprotek, Inc., Spokane, WA (US)

( * ) Notice: Subject to any disclaimer, the term of this patent is extended or adjusted under 35 U.S.C. 154(b) by 0 days.

(21) Appl. No.: 15/561,949

(22) PCT Filed: Mar. 24, 2016

(86) PCT No.: PCT/US2016/024095
§ 371 (c)(1),
(2) Date: Sep. 26, 2017

(87) PCT Pub. No.: WO2016/160531
PCT Pub. Date: Oct. 6, 2016

(65) Prior Publication Data
US 2018/0318515 A1 Nov. 8, 2018

Related U.S. Application Data

(60) Provisional application No. 62/139,582, filed on Mar. 27, 2015.

(51) Int. Cl.
| | | |
|---|---|---|
| *A61M 5/315* | (2006.01) | |
| *A61M 5/00* | (2006.01) | |
| *A61J 1/03* | (2006.01) | |
| *A61M 5/178* | (2006.01) | |
| *A61M 5/50* | (2006.01) | |

(52) U.S. Cl.
CPC ............ *A61M 5/31511* (2013.01); *A61J 1/03* (2013.01); *A61M 5/002* (2013.01); *A61M 5/008* (2013.01); *A61M 5/31501* (2013.01); *A61M 5/178* (2013.01); *A61M 2005/5033* (2013.01); *A61M 2209/06* (2013.01)

(58) Field of Classification Search
CPC .............. A61M 5/31511; A61M 5/002; A61M 5/31501; A61J 1/03
USPC ......................................................... 604/187
See application file for complete search history.

(56) References Cited

U.S. PATENT DOCUMENTS

| | | |
|---|---|---|
| 776,402 A | 11/1904 | Johnson |
| 4,243,035 A | 1/1981 | Barrett |
| 4,429,793 A | 2/1984 | Ehmann |

(Continued)

FOREIGN PATENT DOCUMENTS

| | | |
|---|---|---|
| DE | 1922884 U | 11/1969 |
| WO | WO2013130891 A1 | 9/2013 |
| WO | WO2014144416 | 9/2014 |

OTHER PUBLICATIONS

Office Action for U.S. Appl. No. 15/561,957, dated Jun. 15, 2018, Tennican, "Injection Systems With Storage Compartments", 09 pages.

(Continued)

*Primary Examiner* — Phillip A Gray
(74) *Attorney, Agent, or Firm* — Lee & Hayes, P.C.

(57) ABSTRACT

Injection systems with storage compartments to house various materials are described. The storage compartments facilitate provision of medical care in space- and time-efficient manners and are particularly useful in providing care in non-medical facilities.

18 Claims, 7 Drawing Sheets

(56) References Cited

U.S. PATENT DOCUMENTS

| | | | |
|---|---|---|---|
| 4,657,138 | A | 4/1987 | Watson |
| 5,163,557 | A | 11/1992 | Sokolowski |
| 5,533,625 | A | 7/1996 | Mikkelsen |
| 6,398,027 | B1 | 6/2002 | Ryu |
| 7,753,203 | B2 | 7/2010 | Lampropoulos et al. |
| 1,024,674 | A1 | 4/2012 | Briggs |
| 9,889,248 | B2 | 2/2018 | Head et al. |
| 2004/0069667 | A1 | 4/2004 | Tomellini et al. |
| 2005/0203464 | A1 | 9/2005 | Haider et al. |
| 2006/0079834 | A1* | 4/2006 | Tennican ............ A61J 1/2096 604/88 |
| 2007/0167917 | A1 | 7/2007 | Lee |
| 2008/0086091 | A1* | 4/2008 | Anderson .......... A61M 5/31511 604/192 |
| 2010/0051491 | A1 | 3/2010 | Lampropoulos et al. |
| 2010/0059560 | A1 | 3/2010 | Lanum |
| 2011/0201867 | A1 | 8/2011 | Wagner |
| 2012/0109073 | A1 | 5/2012 | Anderson et al. |
| 2013/0178804 | A1* | 7/2013 | Tennican ............ A61M 39/165 604/218 |
| 2015/0060462 | A1 | 3/2015 | Colbert et al. |
| 2015/0164743 | A1 | 6/2015 | Janson et al. |
| 2016/0030671 | A1 | 2/2016 | Tennican et al. |
| 2018/0110918 | A1 | 4/2018 | Tennican |

OTHER PUBLICATIONS

Barnes, et al., "A Woman's Guide to Diabetes: A Path to Wellness", American Diabetes Association, Nov. 21, 2014; 4 pages.
PCT Invitation to Pay Additional Fees dated May 31, 2016 for PCT Application No. PCT/US16/24095, 2 pages.
PCT Invitation to Pay Additional Fees dated Jun. 8, 2016 for PCT application No. PCT/US16/24089; 2 pages.
PCT Search Report and Written Opinion dated Oct. 20, 2016 for PCT Application No. PCT/US16/24089, 14 pages.
PCT Search Report and Written Opinion dated Aug. 26, 2016 for PCT Application No. PCT/US16/24095, 14 pages.
Extended European Search Report dated Jul. 9, 2018 for European patent application No. 16773809.5, 8 pages.
Extended European Search Report dated Sep. 20, 2018, for European Application No. 16773810.3, 8 pages.

* cited by examiner

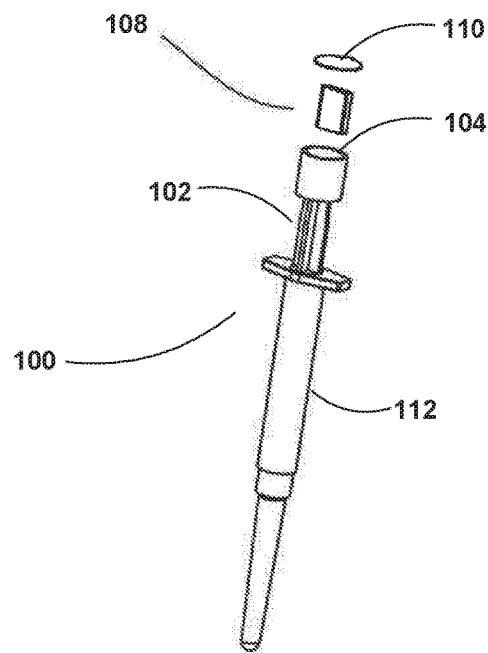 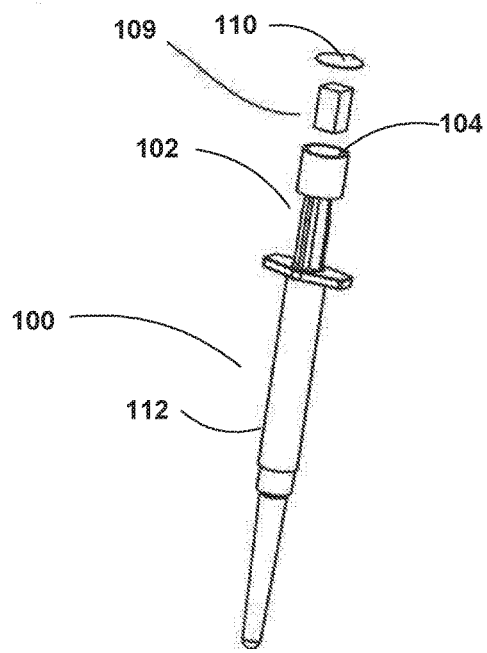
FIG. 2C  FIG. 2D
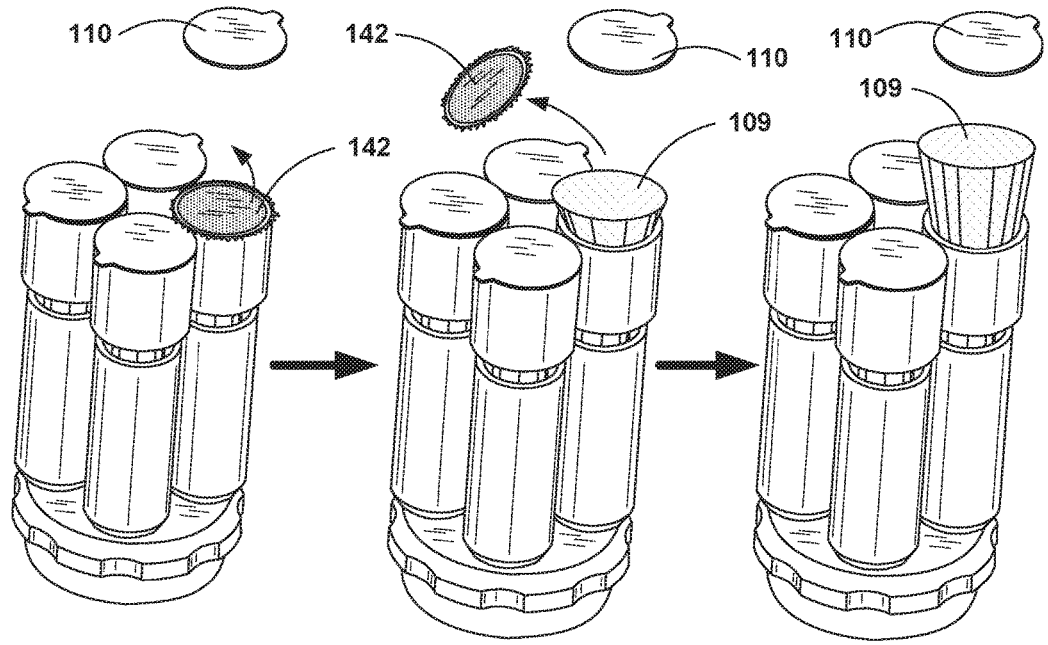
FIG. 2E

INJECTION SYSTEMS WITH STORAGE COMPARTMENTS

CROSS REFERENCE TO RELATED APPLICATIONS

This application is the national stage of International Application No. PCT/US16/24095 filed 24 Mar. 2016, which claims priority to, and the benefit of, U.S. Provisional Application No. 62/139,582, filed Mar. 27, 2015, the entire contents of which are incorporated by reference herein.

FIELD OF THE DISCLOSURE

The disclosure provides injection systems with storage compartments to house various materials. The storage compartments facilitate provision of medical care in space and time-efficient manners and are particularly useful in providing care in non-medical facilities.

BACKGROUND OF THE DISCLOSURE

Time is critical in responding to a number of medical conditions. For example, a person suffering from anaphylactic shock due to an allergy may need medication delivered shortly after a reaction begins. Often, however, the person may be in a location far from a medical facility. Even within medical facilities, reducing the time necessary to treat a patient can enhance treatment outcomes.

SUMMARY OF THE DISCLOSURE

Disclosed herein are injection systems with storage compartments. The systems provide compact medical care that can be carried with a person in the event medical care becomes necessary outside of a medical facility. The systems can also be used within medical facilities to streamline access to medications and supplies that are often used together.

An embodiment disclosed herein includes an injection device including a plunger for a syringe. The plunger can include a storage compartment. A syringe having a plunger with a storage compartment can be provided as an individual syringe or can be linked with one or more additional syringes to form a multi-chambered injection device. When a multi-chambered injection device is provided, one or more of the syringes within the device can include a plunger with a storage compartment.

Each of the embodiments disclosed herein facilitates provision of medical care in non-medical and medical facilities.

BRIEF DESCRIPTION OF THE FIGURES

FIGS. 2A-2E depict plungers with storage compartments associated with syringes. FIGS. 2A-2E depict inclusion of various medications (FIG. 2A (capsule); and FIG. 2B (tablet)) or medical supplies (FIG. 2C (folded antiseptic wipe); FIG. 2D (sponge); and FIG. 2E (compressed sponge)) within the storage compartments.

DETAILED DESCRIPTION

Figure 1:
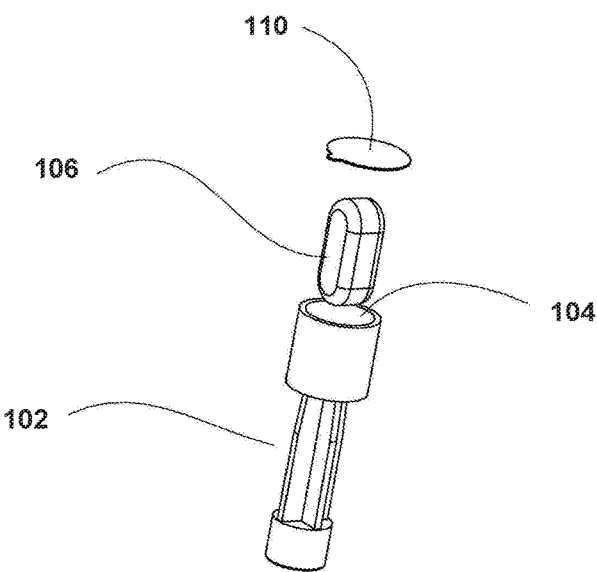
FIG. 1 depicts a syringe plunger with a storage compartment.

Time may be critical for responding to certain medical conditions. For example, a person or animal suffering from anaphylactic shock may need medication delivered shortly after a reaction begins. If the necessary medications and medical supplies are not pre-assembled into an easy-to-access and use configuration, valuable time may be lost. Thus, combining multiple medications, multiple delivery mechanisms of the medications (e.g., intravenous, oral, sublingual, intracardiac), the means to administer the medications, and/or applicators having an antiseptic composition into an easy to use single injection system provides significant benefits.

Disclosed herein are injection systems that facilitate administration of medical treatments by providing injection systems with storage compartments. The injection systems with storage compartments allow various medications and medical supplies to be housed together in space- and use-efficient manners. The space-efficient designs allow more medications and medical supplies to be carried on individuals outside of a medical care facility. The use-efficient designs promote ease of administration, shortening the time required to assemble and safely administer various medications.

The injection systems can be provided to end users without medications pre-provided or pre-loaded. In these embodiments, an end user can select and load medications and supplies into the injection systems. In further embodiments, the injection systems can come with medical supplies, but not medications pre-loaded. In particular embodiments, medical supplies can be housed in the storage compartments. Medical supplies include any object that facilitates administration of a medication, for example, cotton, gauze, bandages, tubing, needles, saline, antiseptic wipes, stents, funnels, sponges, tips, etc. In further embodiments, the injection systems can come pre-loaded with medications but not medical supplies. In still further embodiments, the injection systems can come pre-loaded with medications and medical supplies.

In use the injection systems include a primary medication. A primary medication is one that is intended to treat a medical condition that an end user may experience or encounter. For example, if the end user is prone to severe allergic reactions or is likely to spend time with a person or animal prone to severe allergic reactions, the primary medication could be epinephrine. The primary medication can be housed in a storage compartment or can be pre-loaded into the medication chamber of a syringe.

In other particular embodiments, injection systems can include one or more of a supporting medication, a redundant dose, or a supplemental medication. The supporting medication, redundant dose, and/or supplemental medication can be housed within a storage compartment and/or can be pre-loaded into a medication chamber not housing the primary medication.

A supporting medication is a medication that is not intended to treat the medical condition likely to be experienced or encountered, per se, but nonetheless, provides a beneficial effect that supports the main treatment objective of the primary medication. For example, if the injection system is configured to treat allergic reactions, the primary medication could be epinephrine and the supporting medication could be an antiseptic, an antibiotic, an anti-anxiety medication, or a pain management medication.

A redundant dose is an additional dose of the primary medication. Redundant doses can be provided in the event that the primary dose is unexpectedly not high enough to address the medical condition at issue or in the event that there is a system failure, resulting in incomplete administration of the primary medication dose. Redundant doses can also be provided for treatment regimens where repeated dosing over time is warranted.

A supplemental medication is a second, different medication that is intended to treat the same medical condition that the primary medication is intended to treat. For example, for an allergic reaction, the primary medication could be epinephrine and the supplemental medication could be an antihistamine or a steroid. In particular embodiments, the supplemental medication is intended to treat the same medical condition as the primary medication but through a different mechanism of action.

Embodiments of injection systems disclosed herein include plungers for syringes, syringes, multi-chambered injection devices, and portable kits. Each of these types of injection systems is described more fully in reference to the various figures. The same reference number is used throughout the figures to depict the same or similar feature(s) of the illustrative devices.

FIG. 1 depicts a syringe plunger 102 with a storage compartment 104. A capsule 106 for oral administration is depicted, although as indicated elsewhere, various forms of medications and medical supplies may be housed within the storage compartment 104. The storage compartment can be within the injection device itself or can be independent of the injection device provided elsewhere within the injection system.

In this depicted embodiment, the storage compartment includes a lid 110. The lid 110 can be any mechanism capable of substantially maintaining the housed medication and/or medical supply within the storage compartment 104 so that it is ready for use when needed. Exemplary lid mechanisms include friction-fit caps, snap-caps, screw caps, films, foils, cloths, and covers. In some embodiments, a seal may be used in addition to a lid. In such embodiments, the seal may be in place to maintain sterility of the medication and/or the medical supply. Exemplary seals include films, foils, covers, and the like.

FIGS. 2A-2D depict plungers 102 with storage compartments 104 associated with a medication chamber 112 to form an injection device 100. In the depicted embodiments, the storage compartment includes a lid 110. In various embodiments the injection device can include any plunger, syringe, or syringe system. Exemplary plungers, syringes, and syringe systems include Luer-lock syringes, Air-Tite syringes, syringes made available by Becton Dickinson (Franklin Lakes, N.J.), Allegro Medical, Cole-Palmer, and Catalent, EPI-PEN (Mylan, Canonsburg, Pa.), and Allerject (Sanofi, Laval, Quebec).

Figure 2A:
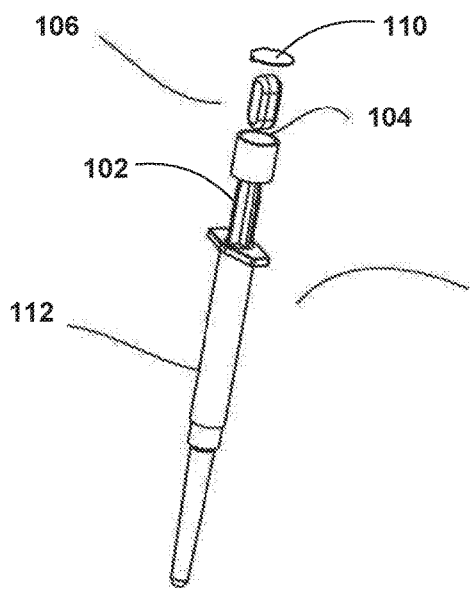
Figure 2B:
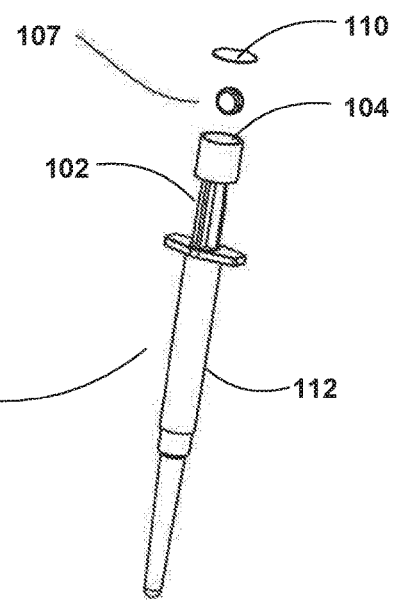

In FIGS. 2A-2D, the depicted medication is a capsule 106 (FIG. 2A) or a tablet 107 (FIG. 2B), and/or the medical supply is an antiseptic wipe 108 (FIG. 2C) or a sponge 109 (FIG. 2D).

As can be seen in FIG. 2E, medical supplies, such as a sponge 109, can be stored in a compressed state, optionally with a seal 142 to maintain sterility under the lid 110. In embodiments where the medical supply is sealed into the storage compartment, the seal may be removed, and the medical supply, such as a sponge, may expand and extend beyond the walls of the storage compartment, as illustrated in FIG. 2E. In some embodiments, the sponge can contain an antiseptic solution or antiseptic gel.

Figure 3:
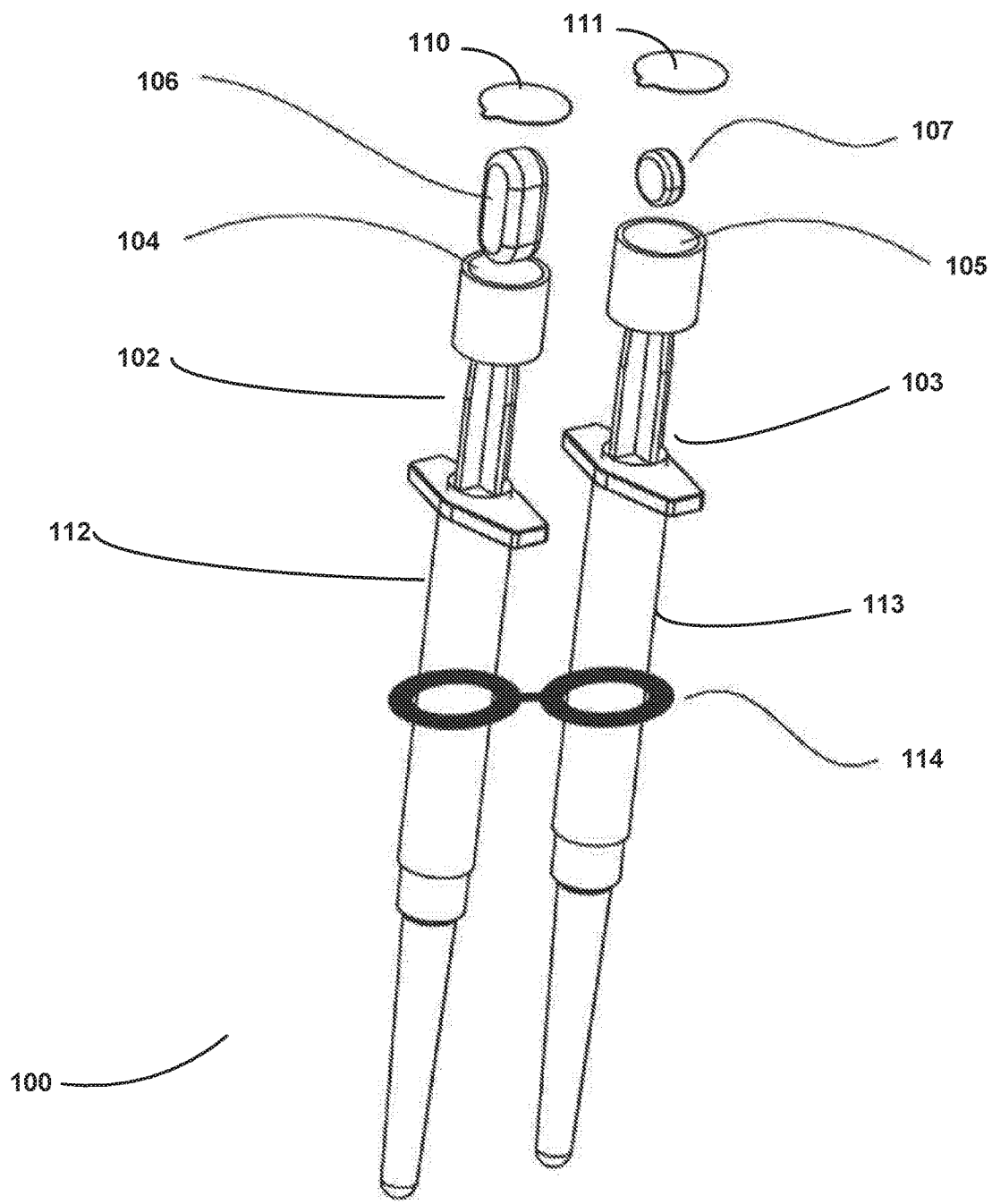
FIG. 3 depicts two syringes including plungers with storage compartments linked to form a multi-chambered injection device.

FIG. 3 depicts a multi-chambered injection device 100 including two syringes that include medication chambers 112, 113 and plungers 102, 103 with storage compartments 104, 105 linked by a linking mechanism 114. In this depicted embodiment, one storage 104 compartment houses a capsule 106 while the second storage compartment 105 houses a tablet 107, and both of the storage compartments include lids 110, 111.

The syringes making up the multi-chambered injection device 100 can be linked by any appropriate linking mechanism 114 such as a housing or a clip. In some embodiments, the syringes may be fused together or formed from a single piece of material. The syringes can be linked by a mechanism 114 that maintains their orientation relative to each other constant or a mechanism 114 that can allow the syringes to move relative to each other. For example, linking mechanism 114 can hold the syringes in a parallel orientation such that both injection needles can be utilized simultaneously, providing two injections at once. Alternatively, the linking mechanism 114 can allow the syringes to rotate lengthwise relative to each other so that only one injection can be provided at a time.

With reference to FIGS. 4A-7, in illustrative implementations, an injection device 100 has one or more of medication chambers 112a, 112b, 112c, 112n (collectively and interchangeably referred to as 112) with each chamber 112 having a proximal end 116, a distal end 118, and a chamber cavity 120 that may have contents pre-loaded therein. The chamber cavities 120 may include a lid 110. The injection device 100 is shown with two or four chambers 112, but the injection device 100 may have a greater or lesser number of chambers 112. The injection device 100 may be prepared and presented to a user with contents already inside of one or more of the chambers 112. The chambers 112 may be generally cylindrical and each chamber may be associated with a plunger 102a, 102b, 102c, 102n (collectively and interchangeably referred to as 102) to expel the contents of the chamber 112 when force is applied to the end of the plunger 102. The contents may be solids, gases, or fluids. The contents may contain single compounds or compositions of multiple compounds. In some embodiments, the contents may be pre-mixed or otherwise prepared for administration before being inserted into the chamber 112. In other embodiments, the contents may be separated by a film or other membrane that is broken when force is applied to the plunger 102. The contents may be medication or other non-medicinal contents such as, for example, saline or water.

Each of the multiple chambers 112 may contain the same or different contents. In some implementations, two or more chambers 112 (such as, for example, 112a and 112b) may contain the same contents while other chambers 112 contain one or more different contents. Providing the same contents (e.g., redundant doses) into more chambers 112 provides redundancy and allows the user to administer a second dose if administration of the contents of one chamber 112 failed. For example, this can provide a backup functionality in case there is a failure either with the injection device 100 or with the use of the injection device 100. In other embodiments, a redundant dose may be used if repeated dosing of a medication is warranted.

Further, separating the same contents into multiple different chambers 112 may allow for simple adjustment of dosage. That is to say, it may be easier for the user, and lead to a more precisely administered dose, to fully dispense the contents of a first chamber 112a and then, if necessary, use the entire contents of a second chamber 112b rather than partially dispensing the contents of a chamber 112a followed by dispensing the remaining contents of the chamber 112a. Because the injection device may have any number of chambers 112, various volumes or dosages may be readily achieved. In various embodiments, dosage can be customized to a particular end-user. For example, dosage can be determined based on body weight, drug clearance rate, age (e.g., infant, pediatric, adult, etc.), and the like.

If one or more of the chambers 112 is pre-loaded there may also be one or more other chambers 112 that are not pre-loaded. Empty chambers 112, if present, may remain unused (e.g., the injection device 100 has four chambers 112 but only three are needed for a particular application), or the empty chambers 112 may be filled by the user at, or shortly before, the time of use.

In one aspect, the injection device 100 may have the chambers 112 pre-loaded with medications intended to be used together to treat a specific medical need. For example, treatment of a strong allergic reaction such as anaphylaxis may be addressed by injection of epinephrine (adrenaline, a primary medication), an antihistamine (a supplemental medication), a steroid (a supplemental medication), an antianxiety medication (a supporting medication), and/or a pain management medication (a supporting medication). The antihistamine may be diphenhydramine or a similar antihistamine. The steroid may be a corticosteroid including cortisone, prednisone, methylprednisolone (MEDROL® (Pharmacia & Upjohn Company LLC, Peapack, N.J.)), and dexamethasone (DECADRON® (Pragma Pharmaceuticals LLC, Locust Valley, N.Y.)).

In one example, a first chamber 112a of the injection device 100 can contain epinephrine, a second chamber 112b of the injection device 100 can contain an antihistamine, a third chamber 112c of the injection device 100 can contain a pain management medication, and a fourth chamber 112d of the injection device 100 may be pre-loaded with another dose of epinephrine (a redundant dose). In this implementation, each of the medications in the chambers 112 of the injection device 100 is related to treatment of the same medical condition, namely allergic reaction. Equipping one injection device 100 with multiple medications can provide a range of anti-allergy therapy (i.e., for anaphylaxis) from quick action/short duration, (epinephrine), to intermediate action/intermediate duration (antihistamine), to longest onset action/greatest duration of activity (corticosteroid). This configuration places different medications suitable for treating different aspects of a severe allergic reaction together in a single device. Thus, in this example, adrenaline may be administered immediately after the reaction begins, the antihistamine may be administered after the patient initially stabilizes, and the corticosteroid may be administered if there is a prolonged delay receiving professional medical care.

Contents of the chambers 112 may be co-administered or may be administered sequentially to a patient. This sequential administration may be in rapid succession or may be delayed. If the sequential administration is delayed, the subsequent medications may be administered based on response of the patient to the previous administered medication or medications.

Contents of the chambers 112 may be administered intramuscularly, subcutaneously, or intravenously with a needle. Contents of the chambers 112 may be administered through an injection or infusion. Injection allows the contents, such as a medication, of the chambers 112 to be quickly mobilized to the bloodstream. Contents of the chambers 112 may be administered intravenously with a coupling to a stent. Contents may also be administered intranasally with an appropriate tip (not shown) coupled to the injection device.

Two or more of the chambers 112 may have the same or different volumes. In some implementations, the volume of one or more chambers 112 may be about 1 mL, about 2 mL, about 5 mL, about 10 mL, about 20 mL, about 30 mL, about 40 mL, about 50 mL, about 60 mL, about 70 mL, about 80 mL, about 90 mL, about 100 mL, about 110 mL, about 120 mL, about 130 mL, or about 140 mL. In other implementations, the volume of one or more chambers 112 may be at least 1 mL, at least 2 mL, at least 5 mL, at least 10 mL, at least 20 mL, at least 30 mL, at least 40 mL, at least 50 mL, at least 60 mL, at least 70 mL, at least 80 mL, at least 90 mL, at least 100 mL, at least 110 mL, at least 120 mL, at least 130 mL, or at least 140 mL. In further implementations, the volume of one or more chambers 112 may be no more than 1 mL, no more than 2 mL, no more than 5 mL, no more than 10 mL, no more than 20 mL, no more than 30 mL, no more than 40 mL, no more than 50 mL, no more than 60 mL, no more than 70 mL, no more than 80 mL, no more than 90 mL, no more than 100 mL, no more than 110 mL, no more than 120 mL, no more than 130 mL, or no more than 140 mL. The volume may be selected based on known volumes of medication suitable for treating a particular medical condition.

Figure 5:
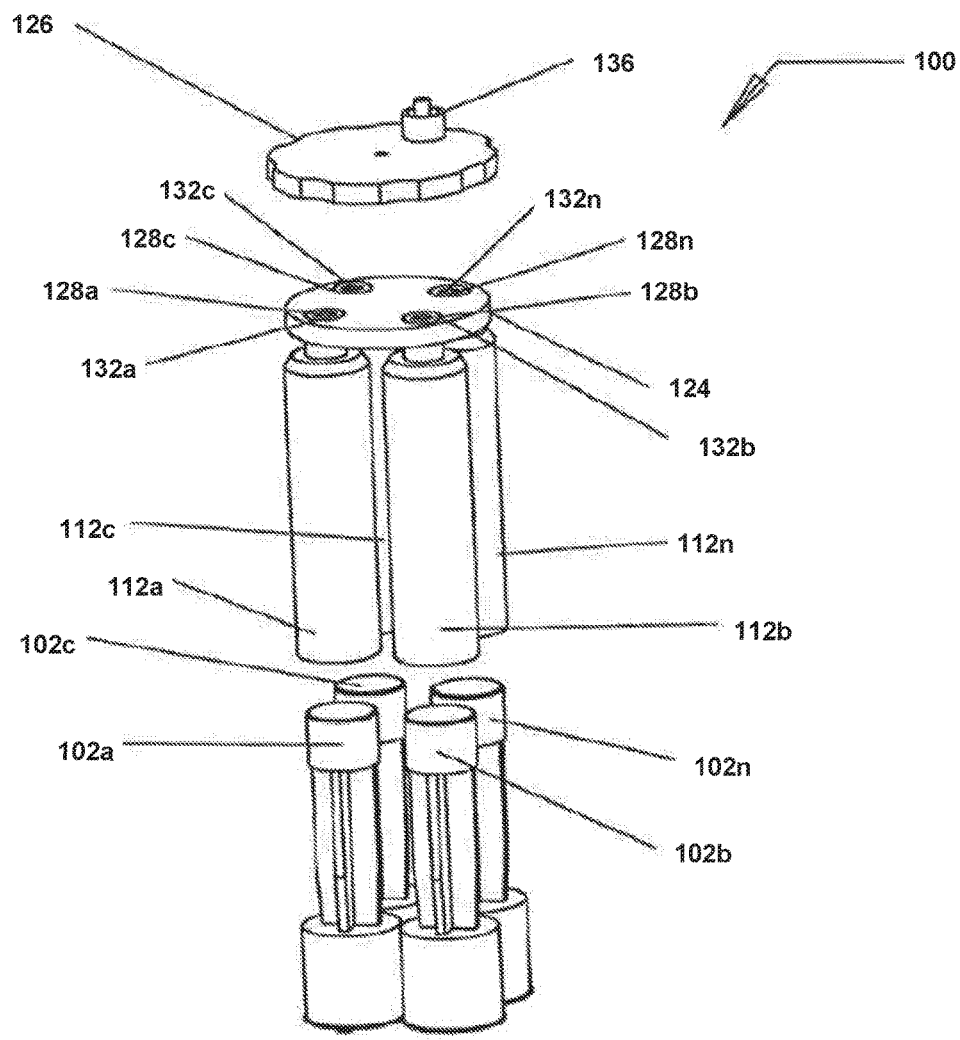
FIG. 5 shows an exploded, isometric view of the multi-chambered injection device of FIG. 4A from a different perspective.

According to an embodiment, an outlet body 122 is connected to the distal end 118 of the chambers 112. According to an embodiment, the outlet body 122 includes a stationary body 124 that is in direct contact with the chambers 112 and a rotatable body 126 that is moveably connected to, or in contact with, the stationary body 124. The distal end 118 of each chamber 112 may be coupled to the stationary body 124 via, for example, a snap fit or screw fit connection (not shown). In other embodiments, the injection device 100 may be manufactured so that the distal ends 118 of the chambers 112 are fused to the stationary body 124. The distal end 118 of each chamber 112 may be connected to the stationary body 124 such that the distal end 118 of each chamber 112 is in communication with an opening 128a, 128b, 128c, . . . 128n (collectively and interchangeably referred to as 128), as shown in FIG. 5.

Figures 4A, 4B:
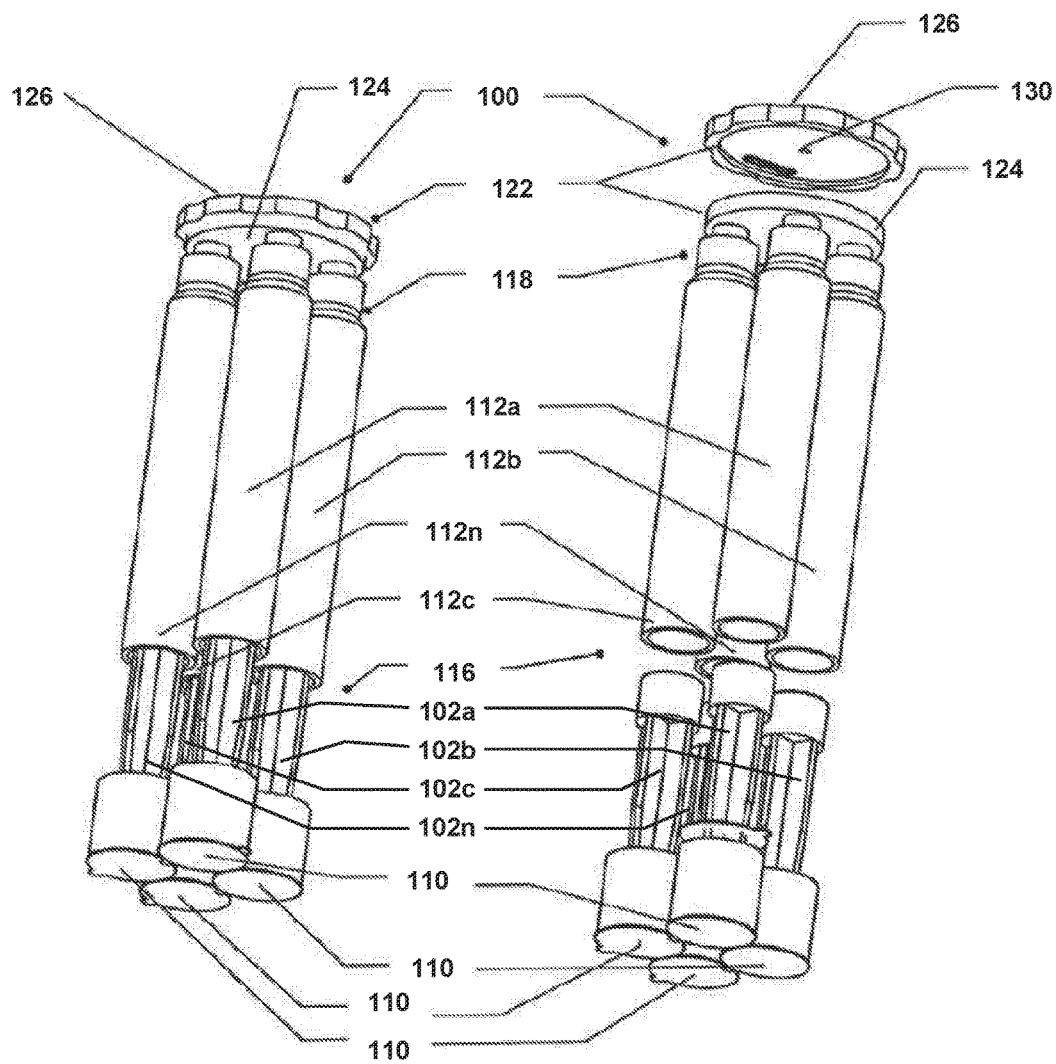
FIG. 4A shows an isometric view of a multi-chambered injection device with multiple plungers each with a storage compartment.
FIG. 4B shows an exploded, isometric view of the multi-chambered injection device of FIG. 4A.
Figure 6:
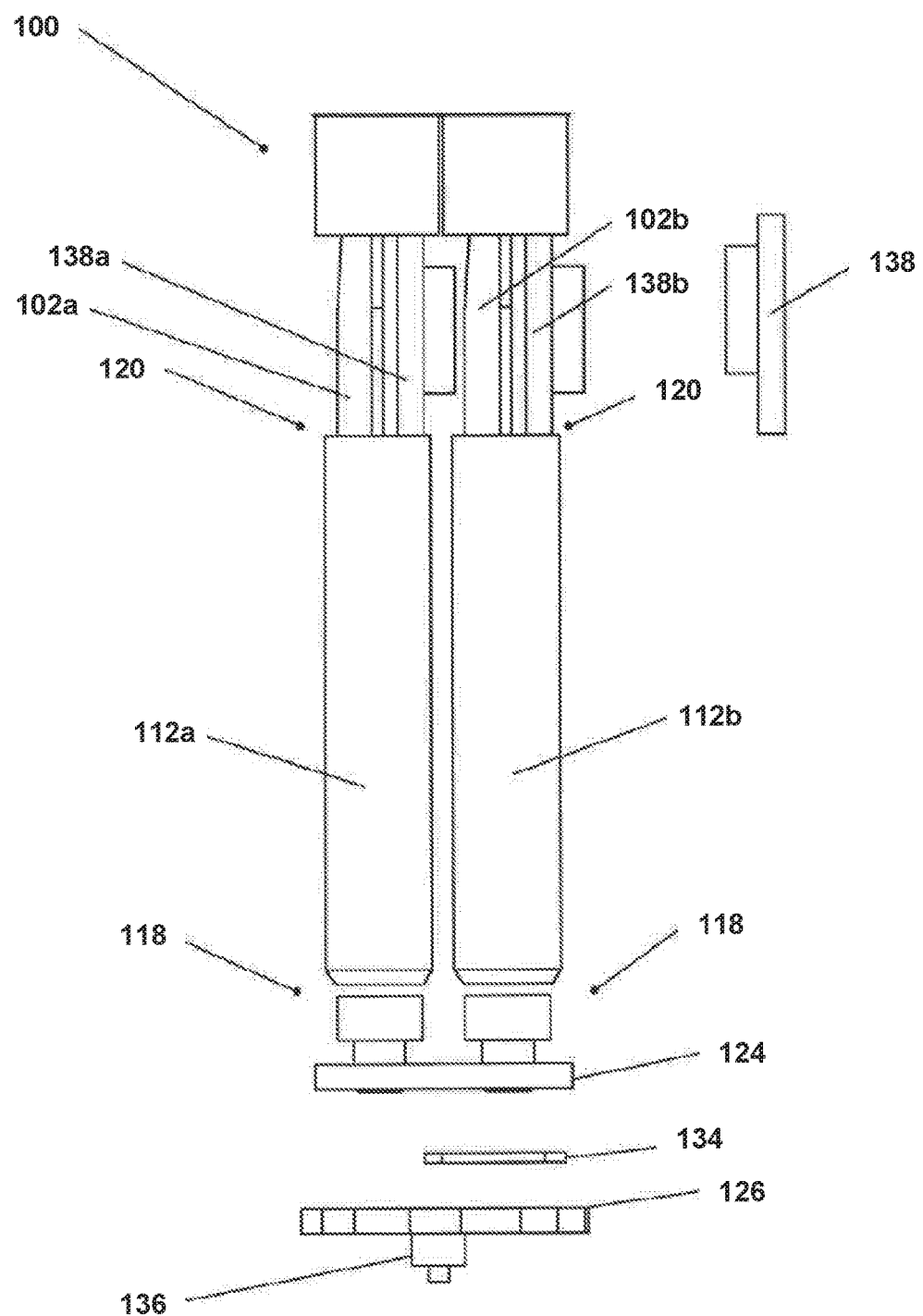
FIG. 6 shows a side view of a multi-chambered injection device with multiple plungers, each with a storage compartment and with a plunger safety lock.
Figure 7:
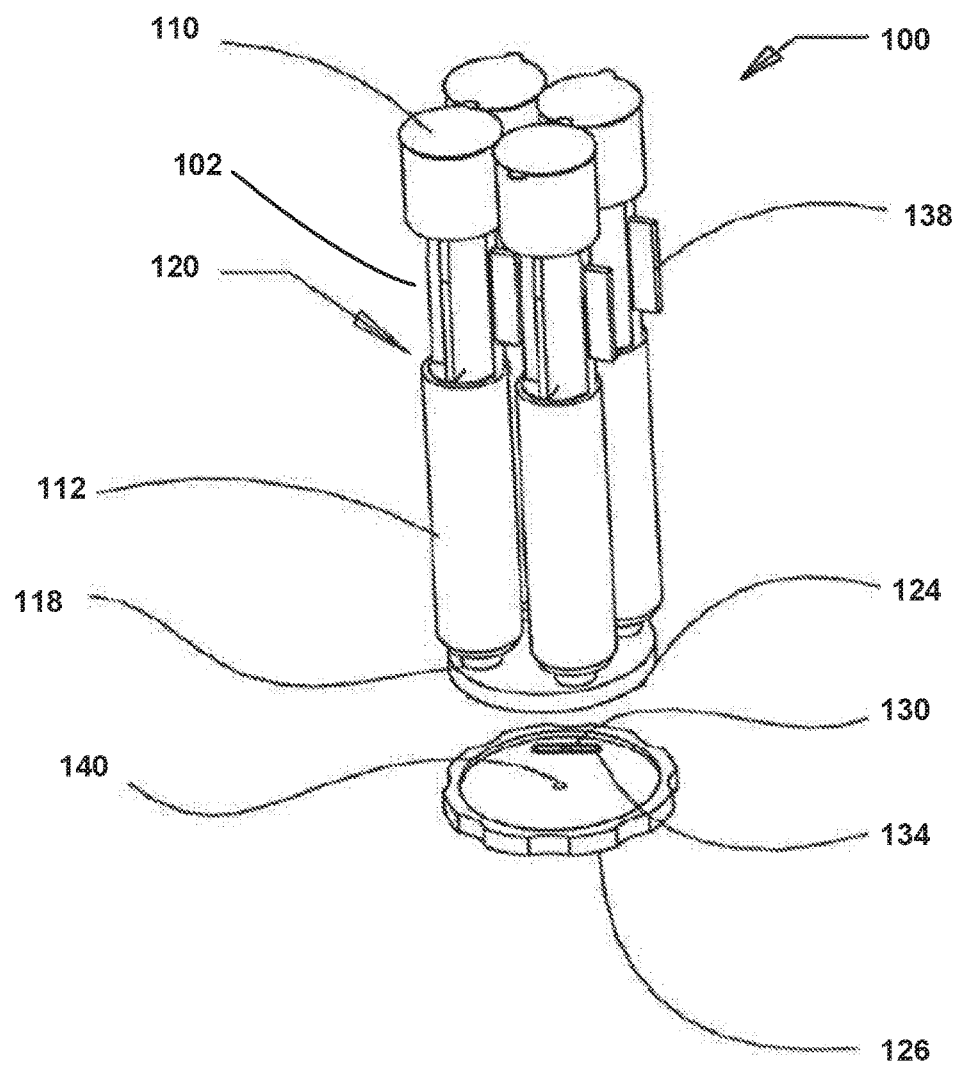
FIG. 7 shows an exploded, isometric view of a multi-chambered injection device with multiple plungers each with a storage compartment and with plunger safety locks and a slit-shaped outlet.

The rotatable body 126 of the outlet body 122 may include one or more outlets 130 which may be aligned with an opening 128 in the stationary body 124 by rotation of the rotatable body 126. According to certain embodiments, the outlet 130 may be in the shape of a circular hole as shown in FIG. 4B or in the form of a slit as shown in FIG. 7. Of course, other suitable shapes could be used. According to certain embodiments, each opening 128 may be surrounded by opening seal 132a, 132b, 132c, . . . 132n (collectively and interchangeably referred to as 132) to help ensure a tight connection between the opening 128 and outlet 130. In other embodiments, such as those as shown in FIGS. 6 and 7, the outlet 130 may be surrounded by an outlet seal 134 to ensure a tight connection between the opening 128 and outlet 130. The outlet 130 may be a hole that is connected to a hollow needle such as a hypodermic needle. In some implementations, the outlet 130 may include a connector 136, such as a tapered connector or a locking connector. The connector 136 may form a fluid-tight seal between the chamber 112 and object (such as, for example, a hypodermic needle or tube) coupled to the other end of the connector 136. Examples of such connectors 136 include a Luer tapered connector, a Luer lock connector, and a Luer slip connector. The other end of the connector 136 may be coupled to a needle with a corresponding (e.g., female) connector. Alternatively, the other end of the connector 136 may be coupled to a catheter or stent.

In some implementations, there may be a single outlet 130 shared by the multiple chambers 112. The chambers 112, which may include medication, may communicate or come in contact with an outlet 130 by rotating or sliding a portion (e.g., rotatable body 126) of the injection device 100. Rotation may be accomplished by the moving the rotatable body 126 relative to the stationary body 124 located at distal end 118 of the chambers 112. Activation may be performed by a user grasping the injection device 100 in two places and twisting the injection device 100 in different directions, as one would do to wring out a washcloth. In some implementations, selection of which chamber 112 to discharge the content of may be performed by this simple mechanism that does not require springs or complex and potentially fallible mechanical devices. For example, an injection device 100 with four chambers 112 may be rotated so that a single outlet 130 or needle (not shown) is aligned with one of the four chambers 112. The other three chambers 112 may be prevented from discharging their contents due to the rotatable body 126 blocking the distal ends 118 of the other chambers 112. Each of the chambers 112 may also be associated with an independent plunger 102. Thus, as a portion of the device is rotated so that the outlet 130 may be aligned with each of the four chambers 112 in turn and the contents of the respective chamber 112 may be dispensed.

The chambers 112 of the injection device 100 may be formed separately and associated with each other through a housing, clip, or other mechanism. Alternatively, multiple chambers 112 may be formed from a single piece of material (e.g., plastic, glass, steel, etc.). Two chambers 112 may be formed as a single piece of material with two cylindrical tubes. Similarly, three chambers 112 may be formed in a generally triangular shaped configuration having three cylindrical tubes within it. As shown in FIG. 4A, the chambers 112 may be in a circular configuration. For example, an injection device 100 with six chambers may have the chambers 112 formed from a single piece of material with six cylinders arranged in a circle around a central axis similar in appearance to a cylinder of a revolver.

Clustered chambers 112 may be used with a shared outlet 130 (e.g., a rotatable hole or slot) or with each chamber 112 having its own outlet 130. In configurations in which each chamber 112 has its own outlet 130, attachments to the outlets 130 such as needles may be placed in a configuration to allow easy and interference-free movement.

As shown in FIG. 6, in some embodiments, the injection device 100 may include a plunger safety lock 138a, 138b, . . . 138n (collectively and interchangeably referred to as 138), for each chamber 112 which prevents each plunger 102a, 102b, . . . 102n, respectively, from being depressed thus preventing premature expulsion of any contents of the chamber(s) 112. According to an embodiment, the plunger safety lock 138 may be removed by, for example, snap removal.

FIG. 7 shows the outlet 130 formed as a slit. FIG. 7 also provides another view of the plunger safety lock 138 applied to each of the four plungers 102 in this example embodiment. A dimple or hole 140 may be placed at or near the center of the rotatable body 126 to facilitate rotation around a central axis of the injection device 100.

Embodiments disclosed herein include methods of making and using the injection devices disclosed herein. The syringes of the injection device can be formed using any suitable materials. The syringes may be fused together or formed from a single piece of material. In some embodiments, the syringes may be formed independently and then linked with a linking mechanism.

Medical supplies, such as an antiseptic wipe or a bandage, may be loaded into a storage compartment of an injection device. In some embodiments, a lid or other seal can be used to cover the opening of the storage compartment. An antiseptic wipe or sponge, for example, can be used to clean an injection site before or after administration of the primary medication. In some embodiments, methods include loading a primary medication into one or more chambers of the injection device. In other embodiments, a primary medication is pre-loaded into one or more chambers of the injection device. In some embodiments, an outlet body and/or a connector may be attached to the distal end of the medication chamber prior to use. A first plunger can then be depressed in order to dispense the primary medication.

Before or after administration of the primary medication, a supporting medication or a supplemental medication may be injected or otherwise administered. In some embodiments, the supporting medication or the supplemental medication are in a formulation which is suitable for administration by the injection device (such as intramuscular injection, intravenous injection, intranasal administration, etc.). In such embodiments, the supporting medication or supplemental medication may be loaded into one or more chambers of the injection device by a user. In other embodiments, the supporting medication or the supplemental medication may be pre-loaded into one or more chambers of the injection device prior to use. In various embodiments, the user may select the desired medication by rotating the rotatable body relative to the stationary body such that the appropriate chamber comes in contact with the outlet prior to exerting force on the plunger. For example, in some embodiments, after a primary medication has been administered from a first chamber, a second outlet can be selected by rotating the rotatable body of the injection device. A second plunger can then be depressed in order to dispense a supporting medication, which, in this example, is also injected.

In other embodiments where a linking mechanism between the syringes allows the syringes to rotate lengthwise relative to each other, the user may select the desired medication by rotating the syringes lengthwise relative to each other such that only one medication is injected at a time. In further embodiments, the injection device may be configured to administer two or more medications simultaneously or near simultaneously. In such embodiments, a user may administer multiple medications at once.

In some embodiments, a medical supply, such as a bandage or gauze may be stored in a storage compartment. In such embodiments, the bandage or gauze may be removed from a storage compartment and used.

In some embodiments, the supporting medication or the supplemental medication may be in a form suited for oral administration, such as a tablet or capsule, and may be stored in a storage compartment of the injection device. In some embodiments, the supporting medication or supplemental medication may be pre-loaded in a storage compartment of the injection device. In other embodiments, the supporting medication or supplemental medication may be loaded in a storage compartment of the injection device by the user. In some embodiments, a lid or other seal can be used to cover the opening of the storage compartment. For example, a capsule containing a supplemental medication formulated for oral administration can removed from a storage compartment and administered.

In embodiments disclosed herein, an injection device can be provided with instructions for use and/or storage. In some embodiments, the instructions can be in the form of written instructions (e.g., a set of numbered steps) and/or graphic representations (e.g., cartoons, line drawings, diagrams, and the like). In various embodiments, the instructions can be on paper and provided with the injection device; on a sticker or stickers attached to the injection device or attached to packaging associated with the injection device; printed on packaging associated with the injection device; or in any other way that would adequately provide the information to a user. In some embodiments, a web address or a scannable code, such as a QR code, that directs the user to a webpage or application containing such instructions can be provided on or with the injection device, such as on paper and provided with the injection device; on a sticker or stickers attached to the injection device or attached to packaging associated with the injection device; or printed on packaging associated with the injection device. In such embodiments, instructional videos, animations, and the like may also be provided.

In particular embodiments, the instructions for use will direct replacement of medications and medical supplies based on shelf-life or expiration dates of medications and supplies that can be used with the embodiment. Instructions can also direct replacement of medications and medical supplies upon use. End users may subscribe to a medication or medical supply replacement service. In these embodiments, medications and/or medical supplies can be sent to the end user upon request and/or upon a schedule. Instructions can also request that end users provide feedback regarding experiences when using embodiments disclosed herein. The described instructions and request for feedback can be provided on paper, a CD-Rom, a website, or any other appropriate method of communication with end users.

In some embodiments, one or more visual indicators may be provided on or with the injection devices disclosed herein, such as on paper and provided with the injection device; on a sticker or stickers attached to the injection device or attached to packaging associated with the injection device; or printed on packaging associated with the injection device. In such embodiments, the one or more visual indicators may indicate information that may be useful to a user, a medical provider, a medical facility, etc., such as the content of an injection device, the content of a medication chamber of an injection device, and/or the content of a storage compartment of an injection device. In embodiments, the one or more visual indicators may indicate dosage, expiration date, or any other information that may be useful to a user, a medical provider, a medical facility, and the like. In some embodiments, the one or more visual indicators can include codes, such as barcodes, QR codes, and the like. In such embodiments, the codes can be used by a user, a medical provider, a medical facility, and the like to track an injection device, to track the content of an injection device, to track the content of a medication chamber of an injection device, to track the content of a storage compartment of an injection device, and the like. A user, a medical provider, a medical facility, etc. may wish to track injection devices and the contents therein for inventory purposes, for example. In further embodiments, the codes can be used to confirm the contents of an injection device, the contents of a medication chamber of an injection device, the content of a storage compartment of an injection device, and the like; or to update the listed contents of an injection device, a medication chamber of an injection device, the content of a storage compartment of an injection device, and the like, in a tracking system.

Particular embodiments of the injection systems disclosed herein are provided with therapeutically effective amounts of medications. More particular embodiments of the injection systems disclosed herein are provided with therapeutically effective amounts of medications to treat allergies, anaphylaxis, or heart conditions.

A therapeutically effective amount includes those that provide prophylactic treatments and/or therapeutic treatments.

A "prophylactic treatment" includes a treatment administered to a person or animal who does not yet display signs or symptoms of a medical condition but is expected to develop them or who displays only early signs or warning symptoms for the development of the medical condition such that treatment is administered for the purpose of diminishing, preventing, or decreasing the risk of the medical conditioning developing at all or developing further. Thus, a prophylactic treatment functions as a preventative treatment against medical conditions.

A "therapeutic treatment" includes treatments administered to a person or animal experiencing a medical condition for the purpose of reducing, controlling, or eliminating the negative effects of the medical condition.

One example of a medical condition that can be treated with the injection systems disclosed herein is allergic reaction. Allergic reactions, include allergic rhinitis, asthma, atopic dermatitis, food allergy, anaphylaxis, and shock. Anaphylaxis and shock are the most severe forms of allergic reaction and, if untreated, can result in death. All of these disorders are mediated, to some extent, by immediate hypersensitivity reactions in which the activation of inflammatory cells leads rapidly to the release of vasoactive mediators, such as histamine, platelet activating factor (PAF), cytokines, and proteolytic enzymes.

Symptoms of allergic reactions include abdominal pain; coughing; cramps; diarrhea; dizziness; eczema; fainting; hives; itching of the mouth, throat, and/or skin; lightheadedness; nasal congestion; nausea; rashes; throat closure; tingling of the mouth, throat, and/or skin; shortness of breath; swelling of the lips, tongue, and/or skin; trouble breathing; vomiting; weak pulse; and/or wheezing. Therapeutically effective amounts in relation to allergic reactions prevent, reduce, control, or eliminate one or more of these symptoms of an allergic reaction.

Exemplary medications that can be used to treat allergic reactions with the injection systems disclosed herein include antihistamines (e.g., ALLEGRA® (Aventisub II Inc., Greenville, Del.), ASTELIN® (Meda Pharmaceuticals Inc., Somerset, N.J.), BENADRYL® (Warner-Lambert Company LLC, Morris Plains, N.J.), CHLOR-TRIMETON® (MSD Consumer Care, Inc., Memphis, Tenn.), CLARINEX® (Merck Sharp & Dohme Corp., Whitehouse Station, N.J.), CLARITIN® (MSD Consumer Care, Inc., Memphis, Tenn.), DIMETANE® (Citron Pharma LLC, East Brunswick, N.J.), ELESTAT® (Boehringer Ingelheim International GMBH, Germany), pheniramine maleate (OCU-HIST™, Pfizer, Inc., New York, N.Y.), OPTIVAR® (Meda Pharmaceuticals Inc., Somerset, N.J.), PATANOL® (Alcon Research, Ltd., Fort Worth, Tx), TAVIST™, XYZAL™, ZYRTEC® (Johnson & Johnson Corp., New Brunswick, N.J.)); decongestants (e.g., AFRIN® (MSD Consumer Care, Inc., Memphis, Tenn.), SUDAFED® (Johnson & Johnson Corporation, New Brunswick, N.J.), NEO-SYNEPHRINE® (Foundation Consumer Healthcare, LLC, Dover, Del.); combination allergy medications (e.g., ALLEGRA-D® (Aventisub II Inc., Greenville, Del.), BENADRYL ALLERGY AND SINUS (Warner-Lambert Company LLC, Morris Plains, N.J.), CLARITIN-D® (MSD Consumer Care, Inc., Memphis, Tenn.), DYMISTA® (Meda Pharmaceuticals Inc., Somerset, N.J.), NAPHCON® (Alcon Research, Ltd., Fort Worth, Tex.), OPTIVAR® (Meda Pharmaceuticals Inc., Somerset, N.J.), PATANOL® (Alcon Research, Ltd. Fort Worth, Tex.), SEMPREX-D® (Actient Pharmaceuticals LLC, Chesterbrook, PN), TYLENOL ALLERGY AND SINUS® (Johnson & Johnson, New Brunswick, N.J.), VASOCON® (Novartis Ag, Basel Switzerland), ZADITOR® (Novartis Ag, Basel, Switzerland), ZYRTEC-D™); steroids (e.g., corticosteroids, ADVAIR® (Glaxo Group, Middlesex, UK), AEROBID® (Forest Laboratories, Inc., New York, N.Y.), ALREX® (Bausch & Lomb Inc., Rochester, N.Y.), ALVESCO® (Takeda GMBH, Germany), ASMANEX® (Merck Sharp & Dohme, Whitehouse Station, N.J.), AZMACORT® (Abbvie Respiratory LLC, Chicago, Ill.), BECONASE® (Glaxo Group, Middlesex, UK), DELTASONE® (Space Age Holdings LLC, Viejo, Calif.), Dexamethasone, FLONASE® (Glaxo Group, Middlesex, UK), FLOVENT® (Glaxo Group, Middlesex, UK), Fluticasone, NASOCORT™, NASONEX® (Merck Sharp & Dohme Corp., Whitehouse Station, N.J.), Prednisone, PULMICORT® (Astrazeneca AB, Sodertalje, Sweden), QNASL® (Teva Respiratory, LLC, Horsham, PN), beclomethasone dipropionate (Q-VAR® (Ivay, LLC, Horsham, Pa.)), RHINOCORT® (Astra Aktiebolag Corp., Sodertalje, Sweden), SYMBICORT® (Astrazeneca AB, Sodertalje, Sweden), VERAMYST® (Glaxo Group Middlesex, UK), ZETONNA® (Takeda GMBH Corporation, Germany)); bronchodilators (e.g., MAXAIR® (Medicis Pharmaceutical Corporation, Scottsdale, Ariz.), PROVENTIL® (Merck Sharp & Dohme Corp., Whitehouse Station, N.J.), PRO-AIR™, VENTOLIN® (Glaxo Group, Middlesex, UK), XOPENEX® (Sunovion Pharmaceuticals Inc., Marlborough, Mass.)); mast cell stabilizers (e.g., ALAMAST® (Santen Pharmaceutical Co., Ltd., Osaka, Japan), ALOCRIL® (Allergan, Inc., Irvine, Calif.), ALOMIDE® (Alcon Research, Ltd, Fort Worth, Tex.), CROLOM® (Bausch & Lomb Inc., Rochester, N.Y.), INTAL® (Fera Pharmaceuticals, LLC, Locust Valley, N.Y.), NASALCROM® (Pharmacia & Upjohn Co., Irvington, N.Y.), sodium cromoglicate (OPTICROM™ Adventis Pharma, Ltd., Surrey, UK), TILADE® (King Pharmaceuticals, Inc., Bristol, Tenn.)); leukotriene modifiers (e.g., ACCOLATE® (Par Pharmaceutical, Inc. Spring Valley, N.Y.) (zafirlukast), SINGULAIR® (Merck Sharp & Dohme Corp. Whitehouse Station, N.J.) (montelukast), ZYFLO® (Chiesi Usa, Inc. Cary, N.C.) (zileuton)); and immunotherapy (e.g., allergy shots, GRASTEK® (Merck Sharp & Dohme Corp., Whitehouse Station, N.J.), ORALAIR® (Stallergenes SA, Antony, France), RAGWITEK® (Merck Sharp & Dohme Corp., Whitehouse Station, N.J.)). Medications described below in relation to anaphylaxis can also be used to treat allergies.

Anaphylaxis refers to a severe, potentially life-threatening systemic hypersensitivity reaction characterized by being rapid in onset with life-threatening airway, breathing, or circulatory problems. It is usually associated with skin and mucosal changes.

Clinical criteria for diagnosing anaphylaxis include presence of any one of the following three criteria: (1) acute onset of an illness (minutes to several hours) with involvement of the skin, mucosal tissue, or both and one or both of the following: (a) respiratory compromise; and (b) reduced blood pressure or associated symptoms of end-organ dysfunction (e.g., hypotonia, syncope, incontinence); (2) two or more of the following that occur rapidly after exposure to a likely allergen: (a) skin or mucosal tissue involvement (e.g., generalized hives, itch-flush, swollen lips, tongue, or uvula); (b) respiratory compromise; (c) reduced blood pressure or associated symptoms of end-organ dysfunction; and (d) persistent gastrointestinal symptoms (e.g., abdominal pain, vomiting); or (3) reduced blood pressure after exposure to a known allergen (minutes to several hours): (a) infants and children: low systolic blood pressure (age specific) or >30% decrease in systolic blood pressure or (b) adults: systolic blood pressure of <90 mmHg or >30% decrease from baseline. Therapeutically effective amounts in relation to anaphylactic reactions prevent, reduce, control, or eliminate one or more of these symptoms of an anaphylactic reaction.

Exemplary medications that can be used to treat anaphylactic reactions with the injection systems disclosed herein include adrenaline, short-acting beta-2 adrenergic agonists (in particular embodiments, inhaled), H1-H4-antihistamines (in particular embodiments, orally administered), corticosteroids, glucocorticosteroids (in particular embodiments, systemic or nebulized), and glucagon. Additional exemplary medications that can be used to treat anaphylactic reactions with the injection systems disclosed herein include H1 antihistamines (e.g., Acrivastine; Azelastine; Bilastine; Brompheniramine; Buclizine; Bromodiphenhydramine; Carbinoxamine; Cetirizine (ZYRTEC® (Johnson & Johnson Corp., New Brunswick, N.J.)); Chlorpromazine; Cyclizine; Chlorpheniramine; Chlorodiphenhydramine; Clemastine; Cyproheptadine; Desloratadine; Dexbrompheniramine; Dexchlorpheniramine; Dimenhydrinate; Dimetindene; Diphenhydramine (BENADRYL® (Warner-Lambert Company LLC, Morris Plains, N.J.); Doxylamine; Ebastine; Embramine; Fexofenadine (ALLEGRA® (Aventisub II Inc. Greenville, Del.)); Hydroxyzine (VISTARIL® (Pfizer, Inc., NY, N.Y.)); Levocetirizine; Loratadine (CLARITIN® (MSD Consumer Care, Inc., Memphis, Tenn.); Meclozine; Mirtazapine; Olopatadine; Orphenadrine; Phenindamine; Pheniramine; Phenyltoloxamine; Promethazine; Pyrilamine; Quetiapine (SEROQUEL® (Astrazeneca UK, London, England)); Rupatadine; Tripelennamine; Triprolidine); H2 antihistamines (e.g., Cimetidine; Famotidine; Lafutidine; Nizatidine; Ranitidine; Roxatidine; Tiotidine); H3 antihistamines (e.g., Clobenpropit; ABT-239; Ciproxifan; Conessine; A-349,821; Thioperamide); H4 antihistamines (e.g., Thioperamide; JNJ 7777120; VUF-6002); atypical antihistamines (e.g., Catechin; Tritoqualine); and mast cell stabilizers (e.g., ALAMAST® (Santen Pharmaceutical Co., Osaka, Japan), ALOCRIL® (Allergan, Inc., Irvine, Calif.), ALOMIDE® (Alcon Research, Ltd., Fort Worth, Tex.), Cromoglicate (cromolyn; CROLOM® (BAUSCH & LOMB INC, Rochester, N.Y.)), INTAL® (Fera Pharmaceuticals, LLC, Locust Valley, N.Y.), NASALCROM® (Pharmacia & Upjohn Co, Irvington, N.H.), NEDOCROMIL™, OPTICROM™, TILADE® (King Pharmaceuticals, Inc, Bristol, Tenn.)).

The following exemplary medications (as well as others in the classes of compounds they represent) can additionally be provided as supporting, redundant, or supplemental medications to those described in the preceding paragraph: ACCOLATE® (Par Pharmaceutical, Inc. Spring Valley, N.Y.) (zafirlukast), ADVAIR® (Glaxo Group, Middlesex, UK), AFRIN® (MSD Consumer Care, Inc., Memphis, Tenn.), AEROBID® (Forest Laboratories, Inc., New York, N.Y.), ALLEGRA® (Aventisub II Inc., Greenville, Del.), ALREX® (Bausch & Lomb Inc., Rochester, N.Y.), ALVESCO® (Takeda GMBH, Germany), ASMANEX® (Merck Sharp & Dohme, Whitehouse Station, N.J.), ASTELIN® (Meda Pharmaceuticals Inc., Somerset, N.J.), AZMACORT® (Abbvie Respiratory LLC, Chicago, Ill.), BECONASE® (Glaxo Group, Middlesex, UK), BENADRYL ALLERGY AND SINUS™, CHLOR-TRIMETON® (MSD Consumer Care, Inc., Memphis, Tenn.), CLARINEX® (Merck Sharp & Dohme Corp., Whitehouse Station, N.J.), CLARITIN-D® (MSD Consumer Care, Inc., Memphis, Tenn.), DELTASONE® (Space Age Holdings LLC, Viejo, Calif.), Dexamethasone, DIMETANE® (Citron Pharma LLC, East Brunswick, N.J.), DYMISTA® (Meda Pharmaceuticals Inc., Somerset, N.J.), ELESTAT® (Boehringer Ingelheim International GMBH, Germany), FLONASE® (Glaxo Group, Middlesex, UK), FLOVENT® (Glaxo Group, Middlesex, UK), FLUTICASONE™, MAXAIR® (Medicis Pharmaceutical Corporation, Scottsdale, Ariz.), NAPHCON® (Alcon Research, Ltd., Fort Worth, Tex.), NASOCORT™, NASONEX® (Merck Sharp & Dohme Corp., Whitehouse Station, N.J.), NEO-SYNEPHRINE® (Foundation Consumer Healthcare, LLC, Dover, Del.), OCU-HIST™, OPTIVAR® (Meda Pharmaceuticals Inc., Somerset, N.J.), PATANOL® (Alcon Research, Ltd., Fort Worth, Tx), prednisone, PRO-AIR™, PROVENTIL® (Merck Sharp & Dohme Corp., Whitehouse Station, N.J.), PULMICORT® (Astrazeneca AB, Sodertalje, Sweden), QNASL® (Teva Respiratory, LLC, Horsham, PN), Q-VAR™, RHINOCORT® (Astra Aktiebolag Corp., Sodertalje, Sweden), SEMPREX-D® (Actient Pharmaceuticals LLC, Chesterbrook, PN), SINGULAIR® (Merck Sharp & Dohme Corp. Whitehouse Station, N.J.) (monteleukast), SUDAFED® (Johnson & Johnson Corporation, New Brunswick, N.J.), SYMBICORT® (Astrazeneca AB, Sodertalje, Sweden), TAVIST™, TYLENOL ALLERGY AND SINUS® (Johnson & Johnson, New Brunswick, N.J.), VASOCON® (Novartis Ag, Basel Switzerland), VENTOLIN® (Glaxo Group, Middlesex, UK), VERAMYST® (Glaxo Group Middlesex, UK), XOPENEX® (Sunovion Pharmaceuticals Inc., Marlborough, Mass.), XYZAL™, ZADITOR® (Novartis Ag, Basel, Switzerland), ZYRTEC-D™, ZETONNA® (Takeda GMBH Corporation, Germany), and ZYFLO® (Chiesi Usa, Inc. Cary, N.C.) (zileuton).

Other examples of medical conditions that can be treated with the injection systems disclosed herein are heart conditions, such as arrhythmias, heart attacks or cardiac arrest. Symptoms of heart conditions include anxiety; chest discomfort; chest pressure or squeezing; dizziness; fatigue; lack of appetite; lightheadedness; loss of consciousness; nausea; pain (e.g., beginning in the chest and spreading to the shoulders, arms, elbows, back, neck, jaw, or abdomen); persistent coughing or wheezing; rapid or irregular pulse; shortness of breath; sweating (e.g., cold sweat); swelling (often in the feet, ankles, legs, or abdomen); vomiting; and/or weakness.

Therapeutically effective amounts in relation to heart conditions, such as heart attacks or cardiac arrest, prevent, reduce, control, or eliminate one or more of these symptoms of a heart condition, addressing the underlying condition leading to the symptom, and/or can preserve heart muscle function following occurrence of the condition.

Exemplary medications that can be used to treat heart conditions with the injection systems disclosed herein include angiotensin-converting enzyme (ACE) inhibitors (e.g., Benazepril (LOTENSIN® (Novartis Pharmaceuticals Corporation, East Hanover, N.J.), Captopril (CAPOTEN® (Phar Pharmaceutical, Inc., Woodcliff Lake, N.J.)), Enalapril (VASOTEC® (Biovail Laboratories Intl., Christ Church, Barbados)), Fosinopril (MONOPRIL® (E. R. Squibb & Sons, L.L.C., Princeton, N.J.)), Lisinopril (PRINIVIL® (Merck Sharp & Dohme Corp., Whitehouse Station, N.J.), ZESTRIL® (Alvogen Pharma US, INC., Pine Brook, N.J.)), Moexipril (UNIVASC® (UCB Mfg., Inc., Rochester, N.Y.)), Perindopril (ACEON® (Biofarma Societe Par Actions Simplifiee, France)), Quinapril (ACCUPRIL® (Warner-Lambert Company, Morris Plains, N.J.)), Ramipril (ALTACE® (King Pharmaceuticals Research And Development, Inc., Cary, N.C.)), Trandolapril (MAVIK® (Abbvie Deutschland Gmbh & Co., Germany)); angiotensin II receptor antagonists (e.g., Candesartan (ATACAND® (AstraZeneca AB, Sodertalje, Sweden)), Eprosartan (TEVETEN® (Abbvie Respiratory LLC, Chicago, Ill.)), Irbesartan (AVAPRO® (Sanofi Societe Anonyme, Paris, France)), Losartan (COZAAR® (Merck Sharp & Dohme Corp., Whitehouse Station, N.J.)), Telmisartan (MICARDIS® (Boehringer Ingelheim KG, Germany)) and Valsartan (DIOVAN® (Novartis Corporation, Summit, N.J.))); anti-arrhythmics (e.g., BETAPACE® (Bayer Pharma Aktiengesellschaft, Germany) (SOTALOL™), CORDARONE® (Sanofi Societe Anonyme, Paris, France) (Amiodarone), Lidocaine, PROCANBID® (Parkedale Pharmaceuticals, Inc., Rochester, Mich.) (Procainamide), TAMBOCOR® (Medicis Pharmaceutical Corp., Scottsdale, Ariz.) (Flecainide)); Anti-coagulants (e.g., Dalteparin (FRAGMIN® (Pfizer Health AB, Stockholm, Sweden)), Danaparoid (ORGARAN® (Aspen Global Incorporated, Grand Bay, Mauritius)), Enoxaparin (LOVENOX® (Aventis Pharma S.A., Antony, France)), Heparin (various), Tinzaparin (INNOHEP® (Leo Pharmaceutical Products Ltd., Ballerup, Denmark), Warfarin (COUMADIN® (Bristol-Myers Squibb Pharma Company, Wilmington, Del.))); Anti-hypotensive/vasopressors (e.g., Sympathomimetics (e.g., Amezinium, Dopamine, Dobutamine, Ephedrine hydrochloride, Epinephrine, Midodrine, Noradrenaline hydrotartrate, Phenylephrine (Mesaton)); Myotropic medications; Angiotensinamide, S-alkylisothiouronium derivatives (e.g., Difetur, Izoturon); Glucocorticoids and mineralocorticoids (e.g., Betamethasone, Dexamethasone, Fludrocortisone, Hydrocortisone, Prednisolone, Prednisone); Analeptics (e.g., Bemegride, Caffeine, *Camphora*, Cordiamine); Psychotropics (e.g., Amphetamine, Atomoxetine, Bupropion, Duloxetine, Methamphetamine, Methylphenidate, Reboxetine, Venlafaxine); Positive inotropic agents (e.g., Amrinone, Cardiac glycosides (e.g., Corglycon, Digoxin, Strophantin K), Milrinone); anti-platelet agents (e.g., Aspirin, Clopidogrel (PLAVIX® (Sanofi Societe Anonyme, Paris, France)), Dipyridamole, Ticlopidine); beta blockers (e.g., Acebutolol (SECTRAL® (Aventis Pharma S.A., Cedex, France)), Atenolol (TENORMIN® (Alvogen Pharma US, Inc., Pine Brook, N.J.)), Betaxolol (KERLONE® (Sanofi Societe Anonyme, Paris, France)), Bisoprolol/hydrochlorothiazide (ZIAC® (Teva Women's Health, Inc., Woodcliff Lake, N.J.)), Bisoprolol (ZEBETA® (Teva Women's Health, Inc., Woodcliff Lake, N.J.)), Carteolol (CARTROL® (Abbvie Inc., Chicago, Ill.), Metoprolol (LOPRES- SOR® (Novartis Pharmaceuticals Corp., East Hanover, N.J.), TOPROL XL® (Astrazeneca LP, Wayne, PN)), Nadolol (CORGARD® (King Pharmaceuticals Research And Development, Inc., Bristol, Tenn.)), Propranolol (INDERAL® (WYETH LLC, London, UK), Sotalol (BETAPACE® (Bayer Pharma, Berlin, Germany), Timolol (BLOCADREN® (Merck Sharp & Dohme CORP, Whitehouse Station, N.J.))); calcium channel blockers (e.g., Amlodipine (NORVASC® (Pfizer, Inc., New York, N.Y.), LOTREL® (Novartis Corp., Summit, N.J.)), Bepridil (VASCOR® (Johnson & Johnson, Corp., New Brunswick, N.J.)), Diltiazem (CARDIZEM® (Valeant Intl., Bermuda), TIAZAC® (Biovail Laboratories Intl., Christ Church, Barbados)), Felodipine (PLENDIL® (Astrazeneca AB, Sodertalje Sweden), Nifedipine (ADALAT® (Bayer Aktiengesellschaft, Germany), PROCARDIA® (Pfizer, Inc., New York, N.Y.)), Nimodipine (NIMOTOP® (Bayer Aktiengesellschaft, Germany)), Nisoldipine (SULAR® (Shionogi Inc., London, UK), Verapamil (CALAN® (G. D. SEARLE & CO., Skokie, Ill.), ISOPTIN® (FSC Laboratories, Inc., Charlotte, N.C.), VERELAN® (Elan Pharma Intl., Westmeath, Ireland)); cholesterol-lowering medications (e.g., Clofibrate, Gemfibrozil, nicotinic acid (niacin), Resins, Statins); diuretics (e.g., Amiloride (MIDAMOR® (Paddock Laboratories, Inc., Minneapolis, Minn.)), Bumetanide (BUMEX® (Validus Pharmaceuticals LLC, Parsippany, N.J.)), Chlorothiazide (DIURIL® (Merck Sharp & Dohme Corp., Whitehouse Station, N.J.)), Chlorthalidone (HYGROTON® (Amneal Pharmaceuticals LLC, Bridgewater, N.J.)), Furosemide (LASIX® (Sanofi-Aventis Deutschland, Frankfurt, Germany), Hydro-chlorothiazide (ESIDRIX® (Ciba-Geigy Corp., Summit, N.J.), HYDRODIURIL™), Indapamide (LOZOL® (Biofarma Corporation, France) and Spironolactone (ALDACTONE® (Pharmacia & Upjohn Company LLC, Kalamazoo, Mich.)); Nitroglycerin; pH elevators (e.g., sodium bicarbonate); and Thrombolytics (e.g., Reteplase, Lanoteplase, tissue plasminogen activator, Staphylokinase, Streptokinase (SK), Tenecteplase, Urokinase).

In various embodiments, dosage can be customized for the subject. In such embodiments, dietary factors, cardiovascular function, gastrointestinal function, liver function, immunologic function, renal function, age, sex, body weight, and the like may be considered. Examples of therapeutically effective amounts to treat conditions can include 0.1 to 5 µg/kg or from 0.5 to 1 µg/kg body weight of a person or animal. In other examples, a dose can include 1 µg/kg, 5 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg or from 0.5 to 1 mg/kg. In other examples, a dose can include 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg or more.

In summary, disclosed herein is an injection system that includes (i) an injection device with a medication chamber; and (ii) a storage compartment. The storage compartment can be within the injection device itself or can be independent of the injection device provided elsewhere within the injection system. The disclosed systems allow a user to easily access and use the curated contents in accordance with standard medical practices. Together, the medication chamber and storage compartment provide: primary medications (e.g., epinephrine to treat an allergic reaction); supporting medications (e.g., an antiseptic to treat the site of administration); redundant doses (e.g., a second dose of epinephrine should the first dose be insufficient); supplemental medications (e.g., a dose of an antihistamine or steroid); and/or medications and materials to support administration of the medications (e.g., one or more medications with needles, sterilizing materials, gauzes, and/or bandages).

Exemplary Embodiments

1. A syringe plunger including a distal end for insertion into a medication chamber of a syringe and a proximal end, wherein the proximal end includes a storage compartment.
2. A syringe plunger of embodiment 1 wherein the storage compartment houses a medication and/or a medical supply.
3. A syringe plunger of any one of embodiments 1 or 2 wherein the medication or medical supply is selected from an anti-histamine, a corticosteroid, an antiseptic, an anti-arrhythmic, a vasopressor, a pH elevator, a needle, a sponge, gauze, tubing, and/or a needle.
4. A syringe including:
a medication chamber with a distal end having an opening through which a medication can be expelled and a proximal end through which a plunger can be inserted; and
a syringe plunger having a distal end for insertion into the medication chamber and a proximal end wherein the proximal end includes a storage compartment.
5. A syringe of embodiment 4, wherein the storage compartment houses a medication and/or a medical supply.
6. A syringe of any one of embodiments 4 or 5, wherein the storage compartment houses an oral medication or a topical medication.
7. A syringe of any one of embodiments 4-6, wherein the medication is epinephrine, an antihistamine, a corticosteroid, an anti-arrhythmic, a vasopressor, a pH elevator, or an antiseptic.
8. A syringe of any one of embodiments 4-7, wherein the storage compartment houses a needle, gauze, sponge, or tubing.
9. A syringe of any one of embodiments 4-8, wherein the storage compartment is covered by a removable seal.
10. A syringe of any one of embodiments 4-9, wherein the removable seal is a cap, foil, or wrap.
11. A syringe of any one of embodiments 4-10, wherein a sponge extends outside of the storage compartment after a seal is removed from an opening on the storage compartment.
12. A syringe of any one of embodiments 4-11, wherein the medication chamber is pre-loaded with a primary medication and the storage compartment houses a supporting medication, a redundant dose, a supplemental medication, and/or a medical supply.
13. A syringe of any one of embodiments 4-12, provided within a kit having separate from the syringe (i) a primary medication and (ii) a supporting medication, a redundant dose, a supplemental medication, and/or a medical supply within the storage compartment.
14. A multi-injection device including at least two syringes, each syringe having a medication chamber with a distal end having an opening through which a medication can be expelled and a proximal end through which a plunger can be inserted, and a plunger, each plunger having a distal end for insertion into a medication chamber and a proximal end, the proximal end of at least one of the plungers having a storage compartment.

15. A multi-injection device of embodiment 14, wherein the syringes are physically linked.

16. A multi-injection device of any one of embodiments 14 or 15, including two, three, or four syringes.

17. A multi-injection device of any one of embodiments 14-16, wherein the medication chambers are connected to an outlet body including an opening for medication release such that the outlet body blocks medication release from all chambers except the chamber aligned with the outlet body opening.

18. A multi-injection device of any one of embodiments 14-17, wherein the outlet body includes a single opening for medication release.

19. A multi-injection device of any one of embodiments 14-18, wherein the outlet body rotates around a central axis.

20. A multi-injection device of any one of embodiments 14-19, wherein the outlet body has a first portion fixedly attached to the medication chambers and a second portion rotatably coupled to the first portion and configured to rotate relative to the first portion around a central axis.

21. A multi-injection device of any one of embodiments 14-20, wherein the syringes are housed within a box or pouch.

22. A multi-injection device of any one of embodiments 14-21, wherein a therapeutically effective amount of a primary medication is provided separate from the syringes within the box or pouch.

23. A multi-injection device of any one of embodiments 14-22, further including within the box or pouch and separate from the syringes a supporting medication, a redundant dose, a supplemental medication and a medical supply.

24. A multi-injection device of any one of embodiments 14-23, wherein one medication chamber is pre-loaded with a therapeutically effective amount of a primary medication; one medication chamber is pre-loaded with a supporting medication, a redundant dose, or a supplemental medication and the storage compartment houses a medical supply.

25. A multi-injection device of any one of embodiments 14-24, wherein one medication chamber is pre-loaded with a therapeutically effective amount of a primary medication; one medication chamber is pre-loaded with a supporting medication, a redundant dose, or a supplemental medication and the storage compartment houses a different supporting medication, a redundant dose, or supplemental medication.

26. A portable kit for the treatment of a condition wherein the portable kit includes at least two syringes associated with a mechanism, a storage compartment, a primary medication, a supporting medication, a redundant dose, a supplemental medication and a medical supply.

27. A portable kit of embodiment 26, wherein the mechanism allows for use of the at least two syringes simultaneously.

28. A portable kit of any one of embodiments 26 or 27, wherein the primary medication is provided in a therapeutically effective amount to treat an allergic reaction or a heart condition.

29. A method including:
obtaining a syringe including a medication chamber with a distal end having an opening through which a medication can be expelled and a proximal end through which a plunger can be inserted, and a syringe plunger having a distal end for insertion into the medication chamber and a proximal end wherein the proximal end includes a storage compartment;
administering a primary medication housed in the syringe to a subject.

30. The method of embodiment 29, wherein storage compartment contains a medical supply, a supporting medication, or a supplemental medication.

31. The method of any one of embodiments 29 or 30, wherein the medical supply is an antiseptic wipe, and the method further includes:
removing the antiseptic wipe from the storage compartment, and
cleaning an injection site of the subject prior to administering the primary medication.

32. The method of any one of embodiments 29-31, further including:
removing the supplemental medication from the storage compartment, and
administering the supplemental medication to the subject.

33. The method of any one of embodiments 29-32, further including:
removing the supporting medication from the storage compartment, and
administering the supporting medication to the subject.

34. A method including:
obtaining a multi-injection device including at least two syringes, each syringe having a medication chamber with a distal end having an opening through which a medication can be expelled and a proximal end through which a plunger can be inserted, and a plunger, each plunger having a distal end for insertion into a medication chamber and a proximal end, the proximal end of at least one of the plungers having a storage compartment;
administering a primary medication housed in a first syringe of the at least two syringes to a subject.

35. The method of embodiment 34, wherein the storage compartment contains a medical supply, a supporting medication, or a supplemental medication.

36. The method of any one of embodiments 34 or 35, wherein the medical supply is an antiseptic wipe, and the method further includes:
removing the antiseptic wipe from the storage compartment, and
cleaning an injection site of the subject prior to administering the primary medication.

37. The method of any one of embodiments 34-36, further including:
removing the supplemental medication from the storage compartment, and
administering the supplemental medication to the subject.

38. The method of any one of embodiments 34-37, further including:
removing the supporting medication from the storage compartment, and
administering the supporting medication to the subject.

39. The method of any one of embodiments 34-38, further including:
administering a content of a second syringe of the at least two syringes to the subject.

40. The method of any one of embodiments 34-39, wherein the content of the second syringe is a redundant dose of the primary medication, a supporting medication, or a supplemental medication.

41. A method of making a multi-injection device, the method including:
forming at least two plungers, a first plunger having a proximal end including a storage compartment;
forming at least two medication chambers; and
inserting a distal end of the at least two plungers into a proximal end of the at least two medication chambers such that at least two syringes are formed.

42. A method of embodiment 41, further including loading a primary medication into a first syringe of the at least two syringes.

43. A method of any one of embodiments 41 or 42, further including loading a redundant dose of the primary medication into a second syringe of the at least two syringes.

44. A method of any one of embodiments 41-43, further including loading a supporting medication or a supplemental medication into a second syringe of the at least two syringes.

45. A method of any one of embodiments 41-44, further including:

inserting a medical supply, a supporting medication, or a supplemental medication into the storage compartment; and covering the storage compartment with the removable seal or lid.

46. A method of any one of embodiments 41-44, wherein the at least two medication chambers are formed in a single piece.

47. A method of any one of embodiments 41-44, wherein the at least two medication chambers are linked by a linking mechanism.

48. A method of any one of embodiments 41-44, wherein the at least two medication chambers are connected to an outlet body including an outlet body opening for medication release such that the outlet body blocks medication release from all chambers except the chamber aligned with the outlet body opening.

As will be understood by one of ordinary skill in the art, each embodiment disclosed herein can comprise, consist essentially of, or consist of its particular stated element, step, ingredient, or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components and to those that do not materially affect the embodiment. As used herein, a material effect would cause a statistically-significant reduction in the ability of a storage compartment to house medication or a medical supply.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the," and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, if references have been made to patents, printed publications, journal articles, and other written text throughout this specification (referenced materials herein), each of the referenced materials are individually incorporated herein by reference in their entirety for their referenced teaching.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of ordinary skill in the art, such as the Oxford Dictionary of Biochemistry and Molecular Biology (Ed. Anthony Smith, Oxford University Press, Oxford, 2004).

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A syringe plunger comprising a distal end for insertion into a medication chamber of a syringe and a proximal end, the proximal end including a storage compartment and a removable lid attached at an opening of the storage compartment for enclosing the storage compartment, the storage compartment and the lid enclosing an orally administered medication.

2. A syringe plunger of claim 1, wherein the medication is selected from an anti-histamine, a corticosteroid, an antiseptic, an antiarrhythmic, a vasopressor, and/or a pH elevator.

3. A syringe comprising:
   a medication chamber with a distal end having an opening through which a medication can be expelled and a proximal end through which a plunger can be inserted; and
   a syringe plunger having a distal end for insertion into the medication chamber and a proximal end the proximal end including a storage compartment and a removable lid attached at an opening of the storage compartment for enclosing the storage compartment, the storage compartment enclosing an orally administered medication.

4. A syringe of claim 3, wherein the storage compartment houses a needle, gauze, sponge, or tubing.

5. A syringe of claim 3, wherein the storage compartment is also covered by a removable seal.

6. A syringe of claim 3, wherein the medication chamber is pre-loaded with a primary medication and the storage compartment houses a medical supply.

7. A syringe of claim 3, provided within a kit having separate from the syringe (i) a primary medication and (ii) a supporting medication, a redundant dose, a supplemental medication, and/or a medical supply within the storage compartment.

8. A multi-injection device comprising at least two syringes, each syringe having a medication chamber with a distal end having an opening through which a medication can be expelled and a proximal end through which a plunger can be inserted, and a plunger, each plunger having a distal end for insertion into a medication chamber and a proximal end, the proximal end of at least one of the plungers having a storage compartment and a removable lid attached at an opening of the storage compartment for enclosing the storage compartment, the storage compartment enclosing an orally administered medication.

9. A multi-injection device of claim 8, wherein the syringes are physically linked.

10. A multi-injection device of claim 8, including two, three, or four syringes.

11. A multi-injection device of claim 8, wherein the medication chambers are connected to an outlet body comprising an opening for medication release such that the outlet body blocks medication release from all chambers except the chamber aligned with the outlet body opening.

12. A multi-injection device of claim 11, wherein the outlet body comprises a single opening for medication release and the outlet body rotates around a central axis.

13. A multi-injection device of claim 11, wherein the outlet body has a first portion fixedly attached to the medication chambers and a second portion rotatably coupled to the first portion and configured to rotate relative to the first portion around a central axis.

14. A multi-injection device of claim 8, wherein the syringes are housed within a box or pouch.

15. A multi-injection device of claim 14, wherein a therapeutically effective amount of a primary medication is provided separate from the syringes within the box or pouch.

16. A multi-injection device of claim 15, further comprising within the box or pouch and separate from the syringes a supporting medication, a redundant dose, a supplemental medication and a medical supply.

17. A multi-injection device of claim 8, wherein one medication chamber is pre-loaded with a therapeutically effective amount of a primary medication; one medication chamber is pre-loaded with a supporting medication, a redundant dose, or a supplemental medication and the storage compartment houses a medical supply.

18. A multi-injection device of claim 8, wherein one medication chamber is pre-loaded with a therapeutically effective amount of a primary medication; one medication chamber is pre-loaded with a supporting medication, a redundant dose, or a supplemental medication and the storage compartment houses a different supporting medication, a redundant dose, or supplemental medication.

* * * * *